United States Patent
Iimura

[19]
[11] Patent Number: 6,094,767
[45] Date of Patent: Aug. 1, 2000

[54] CLEANING APPARATUS USING PHOTOCATALYST

[76] Inventor: Keiji Iimura, 10-8, Akatsuka 3-Chome, Itabashi-ku, Tokyo 175-0092, Japan

[21] Appl. No.: 09/161,013

[22] Filed: Sep. 25, 1998

[51] Int. Cl.[7] .................................................. A46B 15/00
[52] U.S. Cl. ........................... 15/105; 422/22; 604/20; 601/15; 250/504 H
[58] Field of Search .................... 422/22; 15/105, 15/339; 604/20; 601/12; 250/504 H

[56] References Cited

U.S. PATENT DOCUMENTS 3,667,454 6/1972 Prince .
4,526,570 7/1985 Nakagawa et al. .
4,778,173 10/1988 Carr et al. ........................ 15/105 X

*Primary Examiner*—Elizabeth McKane

[57] ABSTRACT

Cleaning apparatus includes a cleaning head, a light source and a light guide. The cleaning head has a flexible contact member including photo-activating catalyst (photocatalyst). The light source emits short wave light rays to activate the photocatalyst. The light guide transmits the light rays from the light source to the contact member(brushes). The cleaning head may have a transparent brush supporter to support a group of brushes with many photocatalyst particles. The light guide may preferably include a transparent rod and/or an optical fiber. The cleaning apparatus may be applied for a vacuum cleaner. Therefore, such dirty component can be cleaned as bacteria, molds etc. by use of the cleaning apparatus of the invention.

20 Claims, 14 Drawing Sheets

FIGURE 5
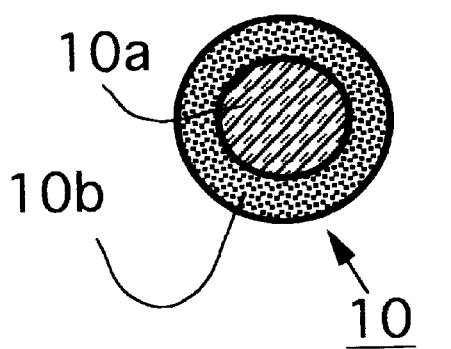
FIG.5A
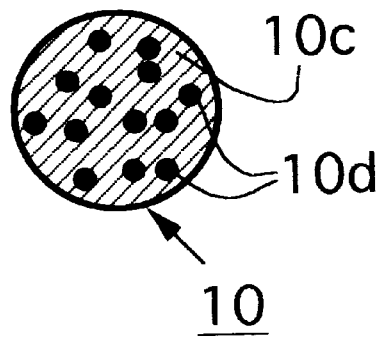
FIG.5B

INVENTOR

KEIJI IIMURA

CLEANING APPARATUS USING PHOTOCATALYST

BACKGROUND OF INVENTION

1. Field of the Invention

The invention relates to a cleaning apparatus for cleaning a substance or a surface of the substance.

2. Description of the Related Art

For cleaning the substance or the surface of the substance, various cleaning apparatuses or cleaning tools are used such as cleaning tool with brushes, vacuum cleaners and mops, according to the substance to be cleaned. The substance to be cleaned, includes a floor, a wall, a tile, a carpet, a bathtub, a sink, cooking utensils and a toilet pot in a house or a building.

In case the substance is a mouth cavity, they brush a surface of teeth, gums and between teeth and gums, in order to clean by using toothbrush and toothpaste.

Dirty component contacted or adhered on the substance to be cleaned (herein after called cleaned substance) includes bust of textile fibers, garbage of foods, nicotine and tar of cigarettes, bacteria, molds, small animals such as flea and tic etc. When the bacteria and molds are adhered on such organic dirty components as the garbage of foods and a dead body of small animal, they increases rapidly and the cleaned substances become dirty more and more according to a lapse of time.

Inside the mouth cavity the dirty components such as a plaque, a bacteria and scale are easy to contact or adhere to teeth. The plaque is a harmful substance that forms on the teeth causing from the bacteria glowing themselves by taking nutriment of the foods garbage and water. The bacteria live in the plaque. The scale is Ca-phosphate caused by combining the plaque and Ca melting in saliva.

However, it is difficult to remove the dirty components such as bacteria and molds only by using the conventional cleaning apparatus or tool. Therefore it is necessary to use a cleaning agent such as soap or a sterilizing agent such as alcohol or cresol, in addition to the conventional cleaning apparatus or tool.

Since plaque is highly adhesive and is not soluble in water, it is necessary to remove the plaque from the teeth by ordinary tooth brushing. And the teeth are easy to become decayed teeth in which enamel of the teeth is dissolved by the plaque. Accordingly, they must go to a dental clinic periodically in order to remove or delete the scale, where the scale fixed on the teeth is physically remove from the teeth by use of special dental tools.

It is known that a photocatalyst activating by light rays with relatively short wave length decomposes or dissolves a substance which is contacted, stacked or closed with the photocatalyst by reaction of oxidation and/or reduction or photocatalyst effect.

Typical photocatalyst is a kind of photo activated semiconductor such as Titan Oxide ($TiO_2$).

In case multiple of photocatalyst particles are used as a form of photocatalyst supported substrate in which a layer including the photocatalyst particlesis fixed and supported on the substrate, the recycle use of photocatalyst particles can be easily done because the separation and collection of the photocatalyst particles are not needed.

The publication of unexamined patent application of Japan No. 155726/1993 discloses that Titan Oxide layer of photocatalyst is coated on a substrate such as metal, ceramics and glass, for the purpose of protecting a surface of the substrate from growth of bacteria.

SUMMARY OF THE INVENTION

It is an object of the present invention is to provide novel cleaning apparatus.

A further object of the present invention is to provide the cleaning apparatus, in which any chemical agents such as cleaning agent and/or sterilizing agent may not be required, in order to sterilize, dissolve and/or remove the dirty components including bacteria and/or molds, contacted or adhered on the surface of any substances.

Therefore, any chemical agents such as cleaning agent and/or sterilizing agent may not be required, in order to dissolve and remove the dirty components including bacteria and/or molds, contacted or adhered on the surface of any substances.

To accomplish the object of the present invention, the cleaning apparatus may comprises a cleaning head which has a flexible contact member including photo-activating catalyst (hereinafter called as "photocatalyst"), a light source which emits short wave light rays capable of activating the photocatalyst, and a light guide member capable of transmitting the shortlight rays from the light source to the flexible contact member.

The light guide member may be comprised of a transparent rod capable of transmitting the short wave light rays. Alternatively, the light guide member may be comprised of an optical fiber or an optical cable capable of transmitting the short wave light rays.

The transparent rod may have a transparent sheath with lower refractive index than that of the transparent rod. Alternatively, the transparent rod may have a light reflective sheath made of a light reflective metal.

The flexible contact member may have a group of brushes including multiple of photocatalyst particles.

At least several brushes among all the brushes may include photocatalyst, so that each brush with photocatalyst is comprised of a core made of organic or inorganic material and a sheath made of organic material, in which the photocatalyst particles are embedded into the sheath. Alternatively, At least several brushes among all the brushes may include photocatalyst, so that each brush with photocatalyst is comprised of a core (or fiber) made of organic material and multiple of photocatalyst particles, in which the photocatalyst particles are embedded into the core.

Such as the light transmitting rod or the optical fiber/optical fiber cable, and they transmit repeatedly based on principle of total reflections (multiple reflections) inside the light guide member toward another terminal of the light guide member. Accordingly, the short wave light rays reach to the cleaning head including photocatalyst in which the photocatalyst is forced to be radiated and activated by them.

Therefore, in case the cleaning head (photocatalyst portion) is contacting or sweeping with the substance to be cleaned (the cleaned substance), the dirty components contacted or adhered on the surface of the cleaned substance are oxidized and/or reduced, dissolved to be cleaned up and become easy to remove or eliminate according to photocatalyst action. Further, a self cleaning effect may be obtained so that the cleaning head itself may be cleaned up also according to the same photocatalyst action.

BRIEF DESCRIPTION OF THE DRAWINGS

A complete understanding of this invention may be obtained from the following explanations, in connection with the accompanying drawings; in which:

FIGS. 5A and 5B illustrate an enlarged cross-sectional view of a piece of brush among a group of brushes 10 in the cleaning head 100, used in first preferred embodiment of the present invention;

DESCRIPTION OF THE PREFERRED EMBODIMENTS

Figure 1:
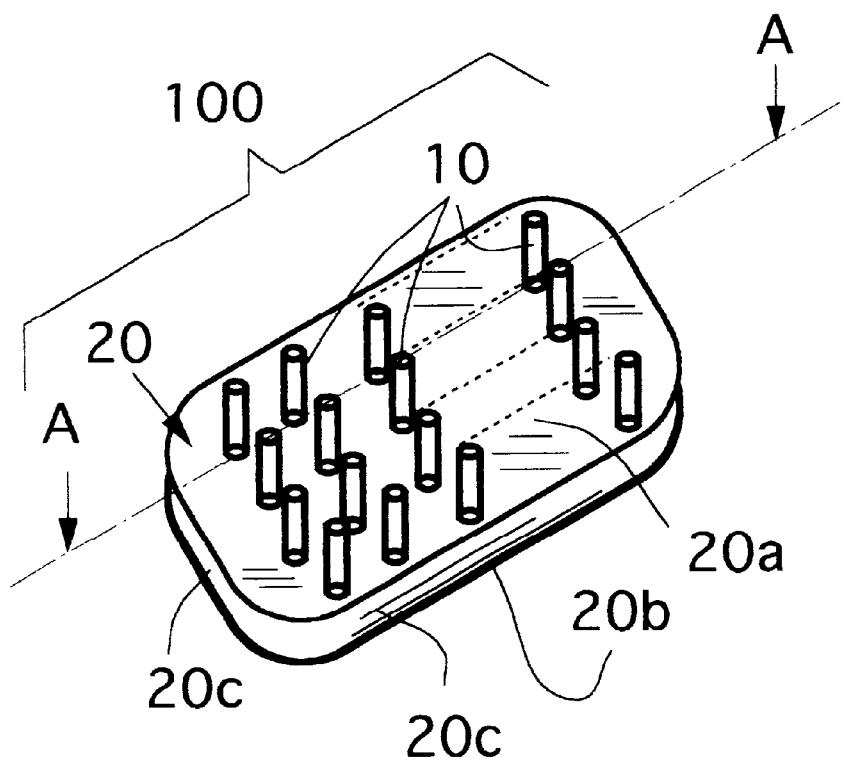
FIG. 1 illustrates a schematic enlarged perspective view of a cleaning head 100 in a cleaning tool 120, explaining first preferred embodiment of the present invention.

The present invention will now be described in detail with reference to the drawings.

In the drawings, a relative dimension or size of each part or portion may be shown as somewhat different one to clarify an explanation of the present invention and the same parts or portions have the same reference numerals.

EMBODIMENT NO.1

Reference is made to FIG. 1, FIG. 2, FIG. 3, FIG. 4 and FIG. 5 showing first preferred embodiment of the present invention.

Figure 2:
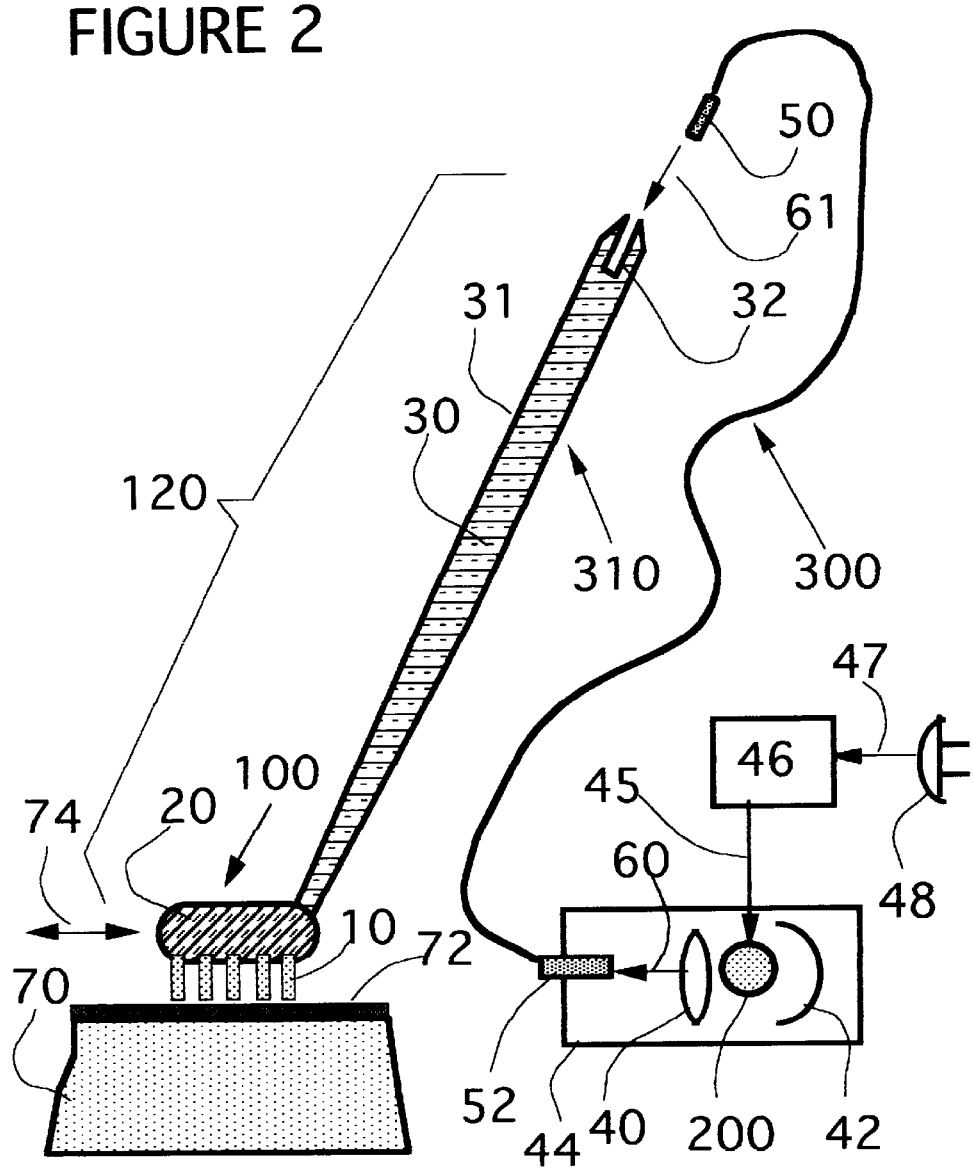
FIG. 2 illustrates a conceptional cross-sectional view of a cleaning apparatus, explaining first preferred embodiment of the present invention.
Figure 3:
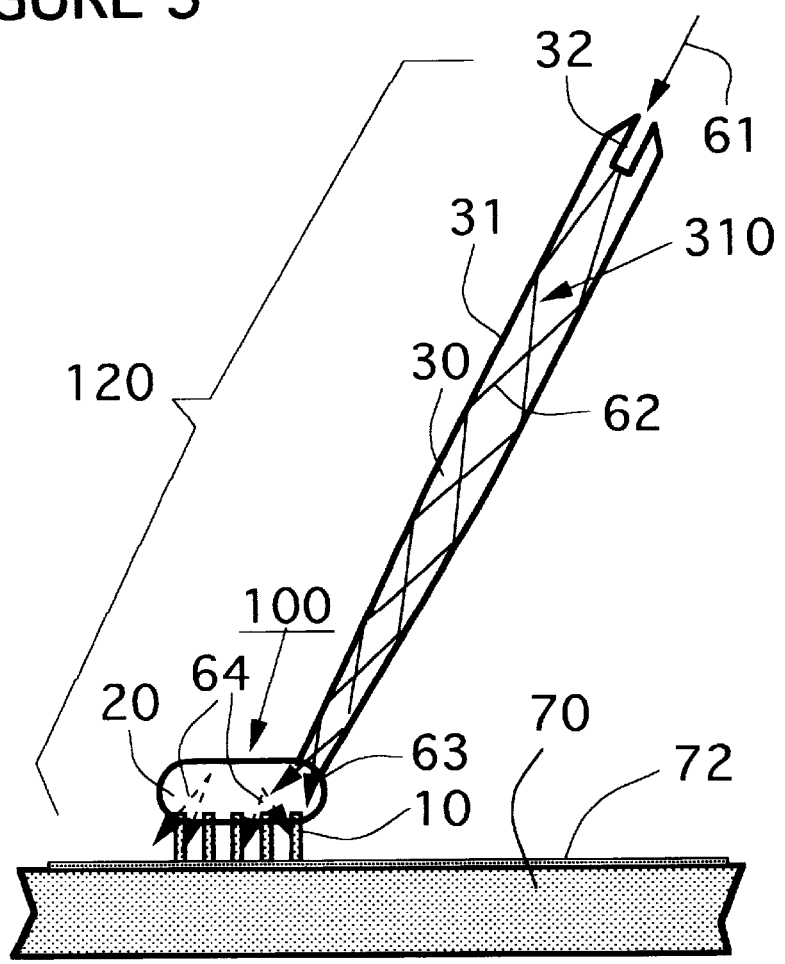
FIG. 3 illustrates a conceptional view of a light transmission passage way in cross-section of the cleaning tool 120 as shown in FIG. 2, explaining first preferred embodiment of the present invention.
Figure 4:
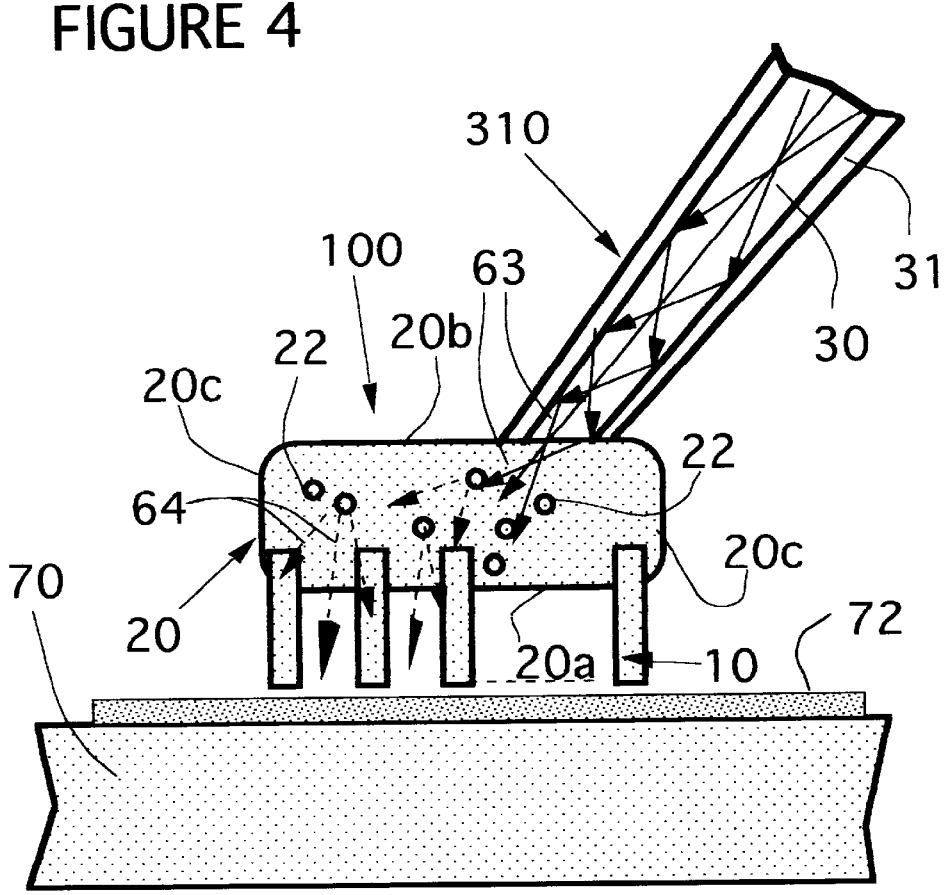
FIG. 4 illustrates a conceptional, partially omitted, enlarged cross-sectional view of the cleaning tool 120 explaining a light transmission passage way in cross-section, explaining first preferred embodiment of the present invention.

FIG. 1 shows a schematic enlarged perspective view of a cleaning head 100 in a cleaning tool 120. FIG. 2 shows a conceptional cross-sectional view of a cleaning apparatus. FIG. 3 shows a conceptional view of a light transmission passage way in cross-section of the cleaning tool 120 as shown in FIG. 2. FIG. 4 shows a conceptional partially omitted enlarged cross-sectional view of the cleaning tool 120 and a light transmission passage way. And FIG. 5 shows an enlarged cross-sectional view of a piece of brush among a group of brushes 10 in the cleaning head 100.

In FIG. 1, FIG. 2, FIG. 3 and FIG. 4, the cleaning apparatus (or cleaning device) 120 is roughly comprised of a cleaning tool 120, a light source 200 and an optical fiber or an optical fiber cable 300. The cleaning tool 120 is further comprised of a cleaning head 100 and handle 310 with rod like shape extending from the cleaning head 100.

The cleaning head 100 may further be comprised of a group of photocatalyst brushes 10 and a transparent brush supporter. The group of photocatalyst brushes 10 may have multiple of brushes in which all or several brushes may include photocatalyst. The transparent brush supporter 20 may fix ends of the photocatalyst brushes 10 and support them. It may be made of transparent material or transparent material embedding many light diffusing elements (particles) 22 (as shown in FIG. 4).

The handle 310 may be provided with a light inlet 32 (as shown in FIG. 2 and FIG. 3) which may be a hole, etc. in the most distant terminal of the handle 310 from the cleaning head 100. It may be comprised of a transparent rod 30 with high refractive index and a transparent layer 31 with low refractive index.

The transparent rod 30 may be coated or covered with the transparent layer 31 around the transparent rod 30. Since the transparent rod 30 is equivalent to a "core" of an optical fiber and the transparent layer 31 is equivalent to a "sheath" (or cl adding) of the optical fiber functionally, the handle 310 is able to transmit almost all light rays effectively within the rod 30 with high transmission factor from the light inlet 32 to the cleaning head 100, according to principle of the optical fiber. Alternatively, a light reflective layer such as aluminum or nickel may be used as a substitute for the transparent sheath (layer) 31 in order to obtain similar high transmission factor.

The brush supporter 20 may be made of transparent material capable of transmitting well ultraviolet rays, such as fused quarts, crystal glass as transparent inorganic materials and acrylic resin, polycarbonate resin, epoxy resin and transparent fluoric resin as transparent organic plastic materials.

For the light diffusing elements 22 in order to give the brush supporter 20 a light diffusing characteristics, conventional white pigments may be used such particles as titanium oxide, aluminum, calcium carbonate and barium carbonate.

Reference numeral 70 indicates an substance to be cleaned (or a cleaned substance) such as floor, carpet and wall in a building or a house, and reference numeral 72 indicates a dirty component which is contacted or adhered on a surface of the cleaned substance 70, as shown in FIG. 2, FIG. 3 and FIG. 4.

The light source 200 emits or generates short wavelength rays including ultraviolet (UV) rays. For the light source 200, various vacuum discharge lamps may be preferably used such as germicidal lamp, black light to cut visible light, UV radiated fluorescent lamp, halogen lamp and conventional fluorescent lamp. A laser to emit coherent UV laser beam may also be used.

The germicidal lamp is conventional low or high pressure mercury lamp using a UV transmissible glass tube such as transparent fused quarts, which emits UV light rays with short wavelength between the range from 250 nm to 280 nm (center wavelength; 253.7 nm) by discharge of mercury.

The black light is a kind of fluorescent lamp emitting blue color and UV light rays using UV transmissible glass tube with a black filter to cut the UV light rays, or using UV transmissible black filter glass tube to cut only the blue color light rays, which emits UV light rays with medium wavelength between the range from 380 nm to 300 nm by discharge of mercury.

The UV radiated fluorescent lamp may be used which uses transparent glass tube without the black filter instead of the black light, which emits blue color light rays and also UV light rays with medium and long wavelength.

The halogen lamp is high pressure mercury lamp adding metal halide inside the lamp tube, which emits UV light rays with medium and long wavelength.

Referring again to FIG. 2, a focus lens 40 and a reflector 42 positioned in rear of the focus lens 40 are installed. The light source 200, the focus lens 40 and the reflector 42 are housed in a light box (or a lamp house) 44. A commercial power is supplied from a power consent 48 to a light control circuit device 46 via an electric cable 47. The light control circuit device 46 controls a lighting of the light source 200. An optical fiber 300 may be comprised of a single number of optical fiber with a transparent core and a transparent sheath capable of transmitting UV light rays and a protective covering. Instead of the optical fiber, an optical fiber cable 300 may be used which is comprised of multiple of optical fibers capable of transmitting UV light rays and a protecting covering. The optical fiber 300 has a pair of optical fiber connectors 50 and 52 in both terminals. A light connector 50 and another light connector 52 of the optical fiber 300 are connected optically with the light inlet 32a of the handle 310 and with a light output of the lamp house 44, respectively.

The UV light rays 60 emitting from the light source 200 are collected at the focus lens 40 and are input at the light connector 52 of the optical fiber 300. The UV light rays 60 incident to the light connector 52 are transmitting in the optical fiber 300 to the light connector 50 and are introduced to the transparent handle 30 via the light inlet 32.

As transmissible materials of short wavelength rays for the optical fiber (core and cladding) 300, the handle 310 and the transparent brush supporter 20, such transparent inorganic materials may be used as Fused Quarts (including more than 99.9 weight % of SiO2), Sapphire, Borosilicate glass (composing SiO2; 75.3, B2O3; 13.8; ZnO; 1.4, Al2O3; 4.3, NaO; 5.0 weight %), etc. And also such transparent organic materials may be used as Acrylic base resin such as Polymethyl methacrylate (PMMA) (refractive index; N≈1.49), Polycarbonate (PC) (N≈1.59) resin, Polyethylene base resin such as Polyethylene terephthalate (PETP) (N≈1.58), Polystyrene (PS) (N≈1.59) and Fluoride base resin such as Polytetra fluoroethylene (PTFE), (N≈1.35), Epoxy resin (EP) (N≈1.55–1.61), etc. It is noted that the core of the optical fiber 300 (or the equivalent members 30 and 20) must be selected from material with comparatively high refractive index, while the cladding of the optical fiber 300 (or the equivalent members 31) must be selected from material with comparatively low refractive index. It is a matter of course that the core must be selected from material with high refractive index, while the sheath must be selected from material with low refractive index.

The UV transmitting optical fiber or cable 300 has been put into market. Such optical fiber capable of transmitting the light rays in ultraviolet region is available from famous cable manufacturers, such as Mitsubishi Cable Industries Ltd., Japan.

For photocatalyst materials including in the photocatalyst brushes 10 of the cleaning head 100, photo activated semiconductors may be used such as Titanium Oxide; TiO2 (photo activation wavelength; not more than 388 nm), Tungsten Oxide; WO2 (photo activation wavelength; not more than 388 nm), Zinc Oxide; ZnO (photo activation wavelength; not more than 388 nm), Zinc Sulfide; ZnS (photo activation wavelength; not more than 344 nm) and Tin Oxide; SnO2 (photo activation wavelength; not more than 326 nm).

Especially the photo-activated titan oxide may be preferably applied for any fields, considering from that an activated power is very high, a life is long, a durability is high and a safety or a harmless to a human body is certified, as it has been used for a long time safely for adding in cosmetics and foods.

Referring again to FIG. 3 and FIG. 4, as the UV transmissible handle 310 is set so that a refractive index N1 of the UV transmissible rod 30 is higher than that N2 of the UV transmissible sheath 31, the UV light rays 61 and 62 are transmitted effectively to the cleaning head 100 repeating multiple reflection. The UV light rays 63 are incident light rays in which the light rays 61 and 62 are transmitting to the UV transmissible brush supporter 20 of the cleaning head 100.

As shown in FIG. 4 (and FIG. 1 & FIG. 3), the cleaning head 100 may have many reflective elements (or reflective particles) 22 which are embedded in the UV transmissible brush supporter 20 in order to give UV light diffusing characteristics. Therefore, the UV light rays 63 incident to the brush supporter 20 are diffused at the reflective elements 22 to become diffusing (scattering) UV light rays 64 and the diffusing UV light rays 84 partially are outgoing outside from a front surface 20a of the brush supporter 20. The outgoing UV light rays 64 are incident to a group of brushes including photocatalyst (photocatalyst brushes) 10 and also incident to the dirty component 72.

The UV light rays 64 incident to the photocatalyst brushes 10 are forced to activate the photocatalyst component so that the dirty component 72 (shown in FIG. 2, FIG. 3 & FIG. 4) is oxidized and/or reduced by photocatalyst action, while the UV light rays 64 incident to the dirty component 72 sterilize directly the dirty component 72 by germicidal effect of the UV light rays 64.

A rear surface 20b and a side surface 20c of the brush supporter 20 excluding the front surface 20a may be preferably coated with light transmissible layer with low refractive index or light reflecting layer in order to obtain more amount of UV light output to the photocatalyst brushes 10.

FIG. 5 indicates an enlarged cross-section of a single brush or a fiber 10A or 10B of the group of photocatalyst brushes 10 in the cleaning head 100, according to a preferred embodiment NO.1.

FIG. 5A indicates one type of the photocatalyst brush or fiber 10. It may be comprised of a composite fiber having a core 10a made of conventional artificial resin fiber (or metal wire) and a sheath including photocatalyst 10b. The sheath is made of conventional artificial resin or rubber in which many photocatalyst particles are embedded. FIG. 5B indicates another type of the photocatalyst brush or fiber 10 which may be comprised of a composite fiber having a core 10c made from a conventional artificial resin or rubber and many photocatalyst particles 10d embedded in the core 10c.

In more detail, in case of FIG. 5A for an example, the photocatalyst brush or fiber 10 may be comprised of a conventional artificial plastic fiber 10a (such as polyester, acrylic and polyimid) or a conventional metal wire 10a (such as steel, stainless steel and titanium) and a sheath 10b coated around the fiber or wire 10a having an artificial plastic compound (such as polyamide; PA, polyethylene; PE, polypropylene; PP, polystyrene; PS, silicone rubber and chloroprene rubber) in which many photocatalyst particles or photocatalyst coated particles are embedded.

In case of FIG. 5B, for an example, the photocatalyst brush or fiber 10 may be comprised of a conventional artificial plastic or rubber fiber 10c (such as polyester, acrylic, polyimid, polyamide; PA, polyethylene; PE, polypropylene; PP, polystyrene; PS, silicone rubber and chloroprene rubber) in which many photocatalyst particles 10d or photocatalyst coated particles 10d are embedded.

Referring to FIG. 2, FIG. 3 and FIG. 3, operation method for the cleaning apparatus of the preferred embodiment NO.1 is mentioned in sequence as follows:

At first, a power consent 48 is inserted into a receptacle of commercial power supply to operate the light control circuit device 44 and to light on the UV light source 200; The optical connector 52 of the optical fiber or cable 300 is optically connected with an optical inlet of the lamp house 44 and another optical connector 50 of the optical fiber or cable 300 is optically connected with an optical inlet 32 of the handle 310 in the cleaning tool 120; The handle 310 of the cleaning tool 120 is gripped by human hands and the brushes 10 of the cleaning head 100 is moved to sweep and make brushing forth and/or back as shown as arrow mark 74 on the surface of the cleaned substance 72 such as floor, carpet, wall and human teeth; and The dirty component 72 as mentioned above can be easily dissolved, removed and cleaned up, because the dirty component 72 is contacted or closed to with the photocatalyst brushes 10 of the cleaning head 100 in which the photocatalyst brushes 10 is activated by radiation of the UV light rays 63 and 64 in order to oxidize and/or reduce the dirty component 72.

Simultaneously, the UV rays 63 incident to the transparent brush supporter 20 are going outside from a front surface of the brush supporter 20 and radiate or illuminate directly the dirty component 72 including such as bacteria, molds etc. on the cleaned substance 70 such as floor, carpet, wall etc., in addition to radiation to the brushes 10.

Therefore, in case the germicidal lamp is preferably used for the UV light source 200, the dirty component 72 including such as bacteria, molds etc. can be sterilized by sterilizing effect of the UV rays.63, 64, because it emits the UV rays between the range from 250 nm to 280 nm (center wavelength; 253.7 nm) exhibiting strong sterilizing effect to bacteria, molds etc.

Accordingly, the dirty component 72 may be dissolved or sterilized indirectly by photocatalyst effect according to activation of the photocatalyst and directly by sterilizing effect according to radiation of the UV rays. In all embodiments of the present invention, the same part or the same member has the same reference numeral. Therefore, in explaining various embodiments to be described below, different portions from the embodiment NO.1 al ready described are explained in detail and the portions al ready described are omitted as much as possible due to simplification of explanation.

EMBODIMENT NO.2

Figure 6:
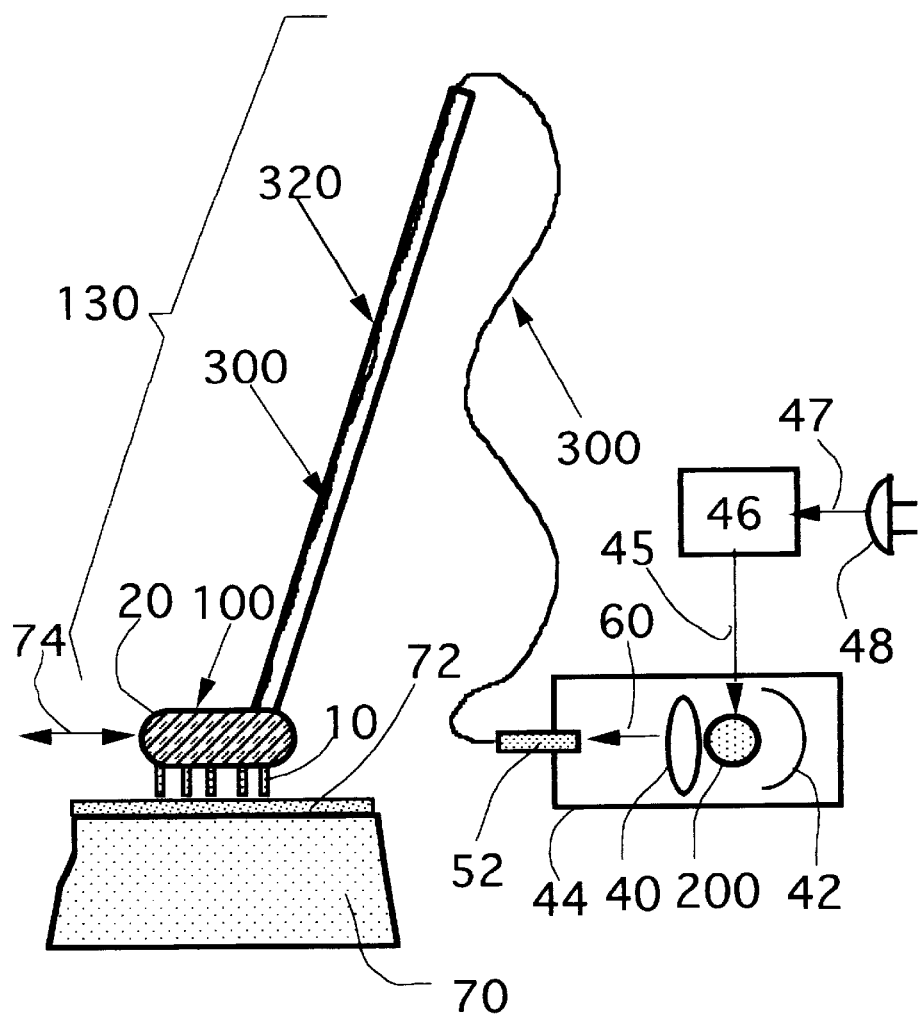
FIG. 6 illustrates a conceptional cross-sectional view of a cleaning apparatus, explaining second preferred embodiment of the present invention.

FIG. 6 shows second preferred embodiment of the present invention, in which a cleaning apparatus is roughly comprised of a cleaning tool 130, a light source 200, a light control circuit device 46 and an optical fiber 300.

The cleaning tool 130 is further comprised of a cleaning head 100 and a handle 320. The handle 320 is formed as a pipe of hollow tube and it is extended from the cleaning head 100 or it is connected with the cleaning head 100. A cleaning head 100 is further comprised of a group of brushes with photocatalyst 10 (photocatalyst brushes) and a transparent brush supporter 20 by which the photocatalyst brushes 10 is fixed. Many light diffusing elements or particles 22 (shown in FIG. 4) may preferably be embedded in the transparent brush supporter 20.

In the embodiment NO.2, one terminal of the optical fiber 300 is connected to the cleaning head 100 by such as an optical fiber connector. The optical fiber 300 is passing inside through the handle of tube 320 and is going outside and is finally connected to a light output part of a lamp house 44 by a detachable optical or light connector 52 of the optical fiber 300.

UV light rays 60 emitting from the light source 200 are gathered by a focus lens 40 and, are input to the optical fiber 300 through the optical connector 52 and are arrived in the cleaning head 100 through the optical fiber 300. In the embodiment NO.2, efficient UV rays transmission is obtained with minimum transmission loss, due to use of UV transmissible optical fiber as mentioned in the embodiment NO.1.

EMBODIMENT NO.3

Figure 7:
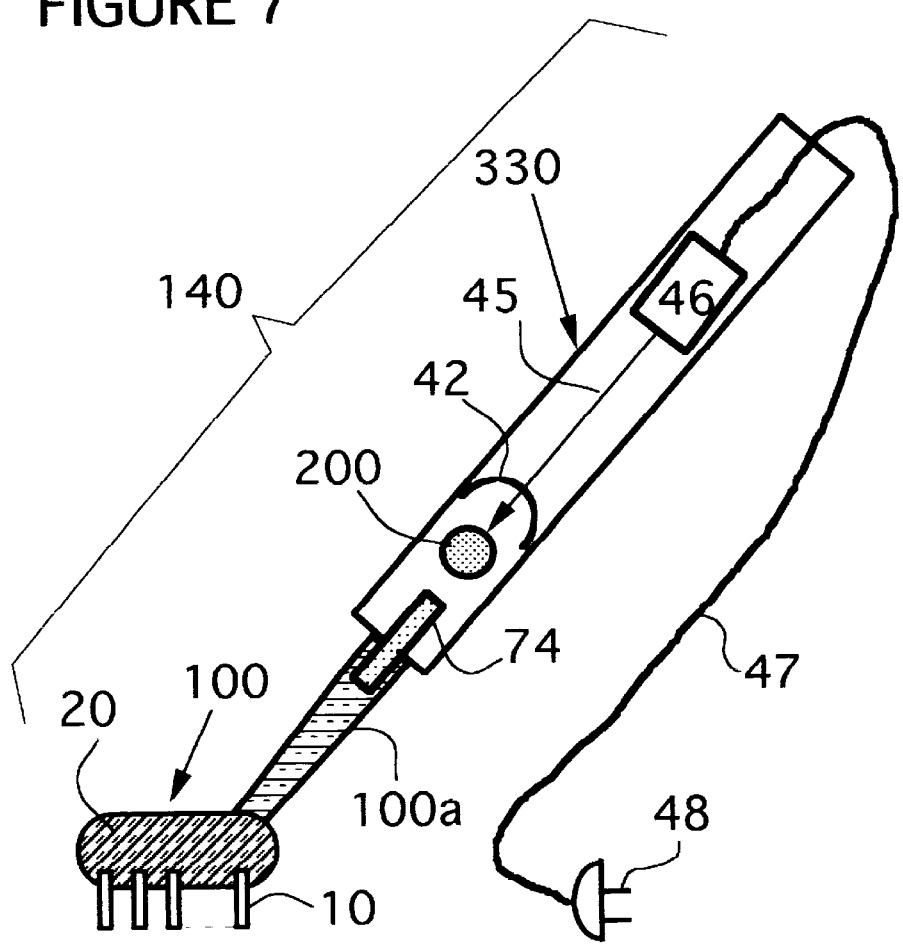
FIG. 7 illustrates a conceptional cross-sectional view of a cleaning apparatus, explaining third preferred embodiment of the present invention.

FIG. 7 shows third preferred embodiment of the present invention, in which a cleaning apparatus is roughly comprised of a cleaning tool 140, a light source 200 and a light control circuit device 46.

The cleaning tool 140 is further comprised of a cleaning head 100, a transparent neck 100a of a part of the cleaning head 100 and a handle 330. The handle 330 is formed as a pipe of hollow tube and it is extended from the transparent neck 100a, which is enlarged as taper shape in cross-section toward the handle 330.

A cleaning head 100 is further comprised of a group of brushes with photocatalyst 10 (photocatalyst brushes) and a transparent brush supporter 20 by which the photocatalyst brushes 10 is fixed. Many light diffusing elements or particles 22 (shown in FIG. 4) may preferably be embedded in the transparent brush supporter 20.

In the embodiment NO.3, a cleaning tool 140, a light source 200, a light control circuit device 46 and a reflector 42 are housed in a hollow portion of the handle 330. light rays emitting from the light source 200 are optically connected and mechanically fixed with the transparent neck 100a via an optical connector 74.

The light control circuit device 46 is electrically connected with an electric cord 47, an electric power supply is fed to the light control circuit device 46 via a power consent 48 and the light source 200 is lit on by an power output of the light control circuit device 46. UV light rays emitting from the light source 200 are gathered by the reflector 42 and introduced into a transparent brush supporter of the cleaning head 100 through the optical connector 74 and the transparent neck 100a. In the embodiment NO.3, the cleaning apparatus becomes very compact, as al most all components of the cleaning apparatus are accommodated in the cleaning tool 140.

EMBODIMENT NO.4

Figure 8:
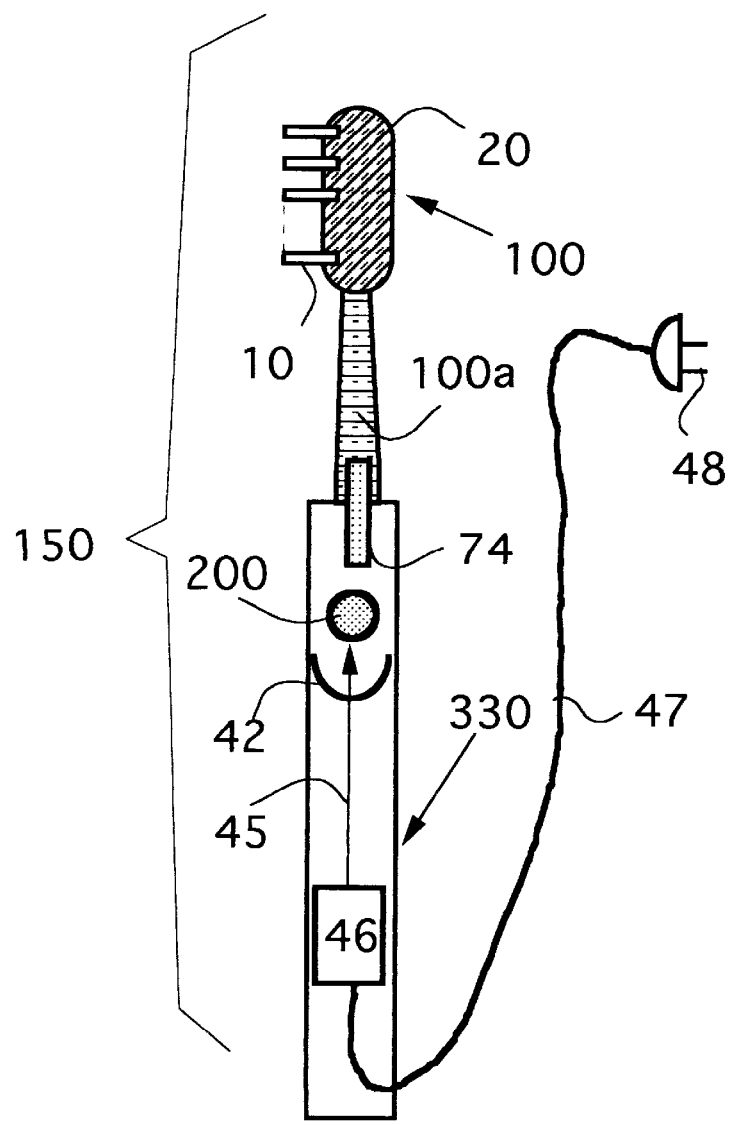
FIG. 8 illustrates a conceptional cross-sectional view of a cleaning apparatus 150, explaining fourth preferred embodiment of the present invention.
Figure 9:
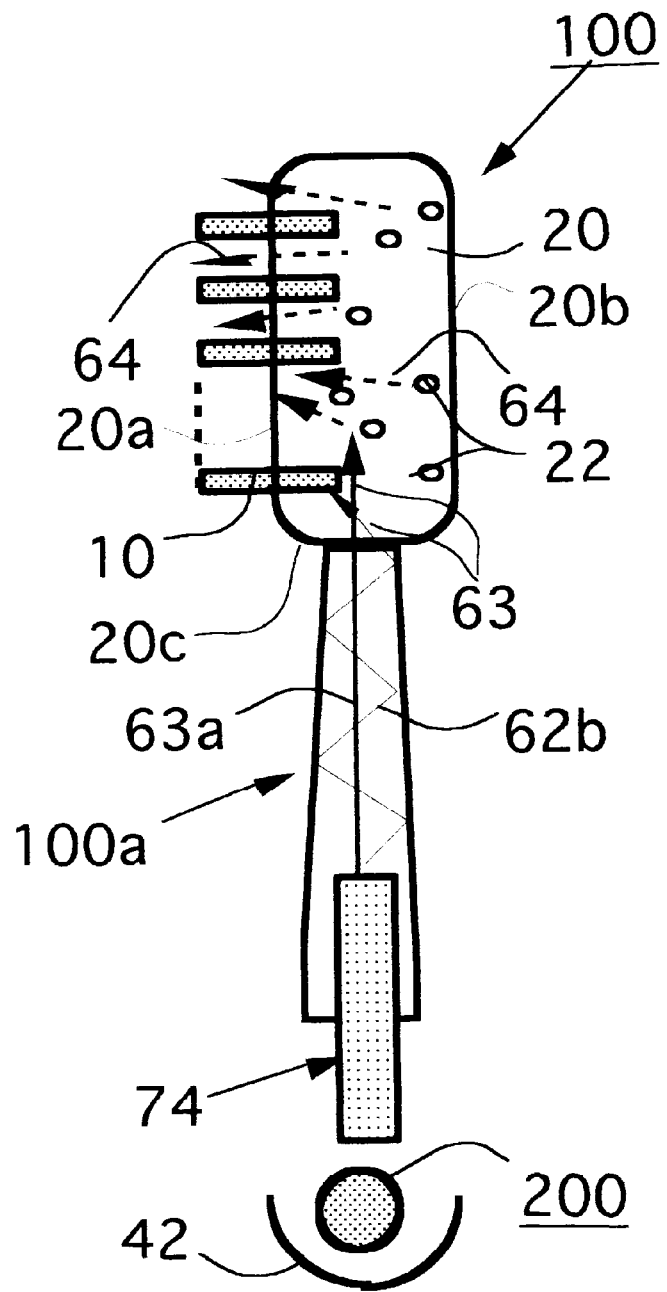
FIG. 9 illustrates a conceptional, partially omitted, enlarged cross-sectional view of the cleaning apparatus 150 and also a light transmission passage way as shown in FIG. 8, explaining fourth preferred embodiment of the present invention.

FIG. 8 and FIG. 9 shows third preferred embodiment of the present invention. A cleaning apparatus is roughly comprised of a cleaning tool 150, a light source 200 and a light control circuit device 46, similar to the embodiment NO.3. The cleaning tool 150 is further comprised of a cleaning head 100, a transparent neck 100a of a part of the cleaning head 100 and a handle 330. The handle 330 is formed as a pipe of hollow tube in which the light source 200, the light control circuit device 46 and a ref lector are accommodated inside the hollow tube. UV light rays generating from the light source 200 are collected by a reflector 42 and are incident to the transparent neck 100a of taper shape. The light rays arrived at the he transparent neck 100a are transmitting directly to a transparent brush support 20 of the head 100 or transmitting by repeating multiple reflection 26 to the brush support 20. Incident light rays 63 into the brush supporter 20 are striking to much light diffusing particles 22 embedded in the brush supporter 20 and becomes diffusing light rays 64. The diffusing light rays 64 radiate photocatalyst brushes 10 by which the brushes are activated to oxidize and/or reduced.

EMBODIMENT NO.5

Figure 10:
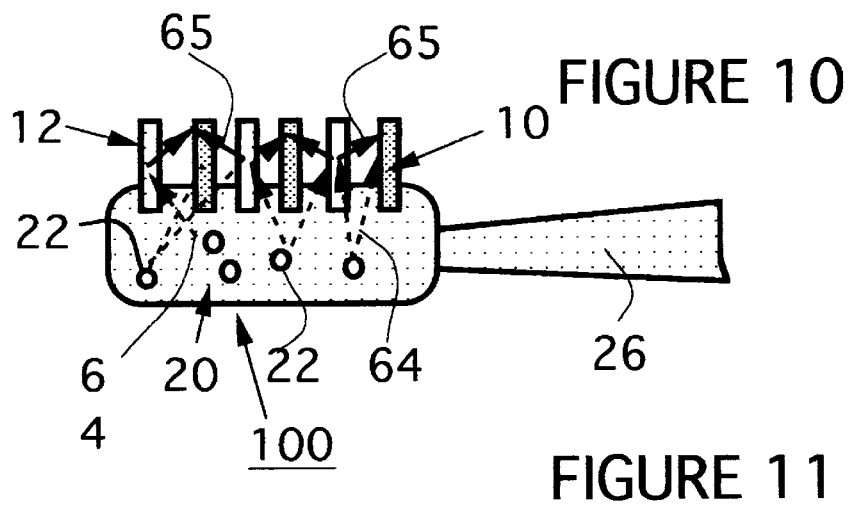
FIG. 10 illustrates a conceptional, partially omitted, enlarged cross-sectional view of a cleaning head 100, explaining fifth preferred embodiment of the present invention.

In FIG. 10 showing fifth preferred embodiment of the present invention, only blush portion of a cleaning head 100 is varied from other embodiments. The cleaning head 100 is comprised of a transparent brush supporter 20, many light diffusing particles 22 embedded in the supporter 20 and the two kinds of brushes consisting of photocatalyst brushes with photocatalyst 10 and transparent brushes without photocatalyst 12. In the embodiment NO.5, Light diffusing rays 64 radiate directly the photocatalyst brushes 10 or radiate indirectly the photocatalyst brushes 10 through the transparent brushes without photocatalyst 12.

EMBODIMENT NO.6

Figure 11:
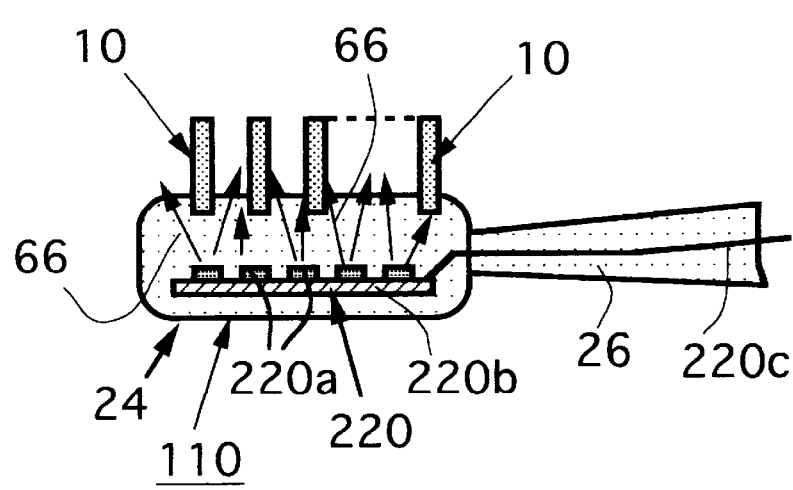
FIG. 11 illustrates a conceptional, partially omitted, enlarged cross-sectional view of a cleaning head 110, explaining seventh preferred embodiment of the present invention.

In FIG. 11 showing seventh preferred embodiment of the present invention, a cleaning head 110 is comprised of a photocatalyst brushes 10 and a brush supporter 24 and a semiconductor light source 220 having a printed wire board 220b and a solid state or light emitting diode (LED) or diodes 220a capable of emitting short wavelength rays. The semiconductor light source 220 is embedded in transparent resin of the brush supporter 24 and an electric power is supplied from lead wires 220c to the light source 220. In this case, very small size of cleaning apparatus is obtained for use on tooth brushing, etc.

EMBODIMENT NO.7

Figure 12:
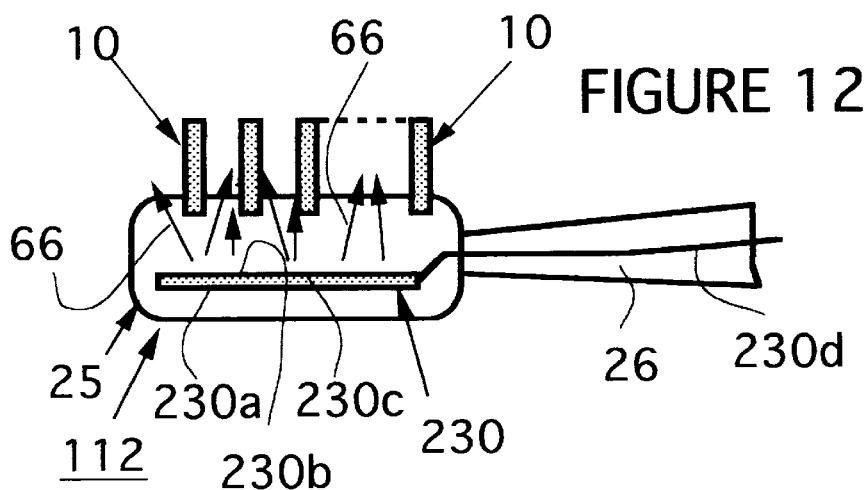
FIG. 12 illustrates a conceptional, partially omitted, enlarged cross-sectional view of a cleaning head 112, explaining eighth preferred embodiment of the present invention.

In FIG. 12 showing seventh preferred embodiment of the present invention, a cleaning head 112 is comprised of a photocatalyst brushes 10 and a brush supporter 25 and a semiconductor light source 230 having a light emitting layer 230c sandwiched by an electrode 230a and a transparent electrode 230a capable of emitting short wavelength rays. The semiconductor light source 230 is embedded in transparent resin of the brush supporter 25 and an electric power is supplied from lead wires 230d to the light source 230. In this case, very small size of cleaning apparatus is obtained for use on tooth brushing, etc.

EMBODIMENT NO.8

Figure 13:
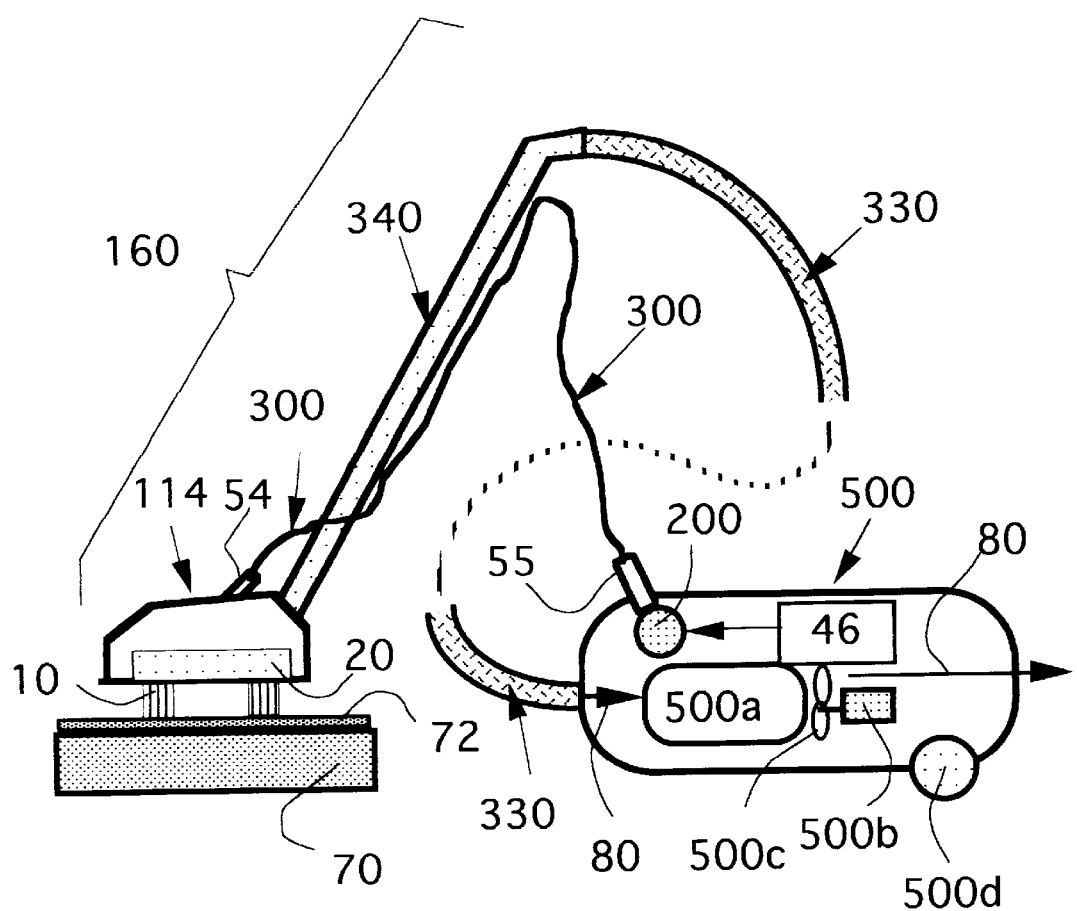
FIG. 13 illustrates a conceptional cross-sectional view of a cleaning apparatus; explaining tenth preferred embodiment of the present invention, in which the invention is applied to a vacuum cleaner.
Figure 14:
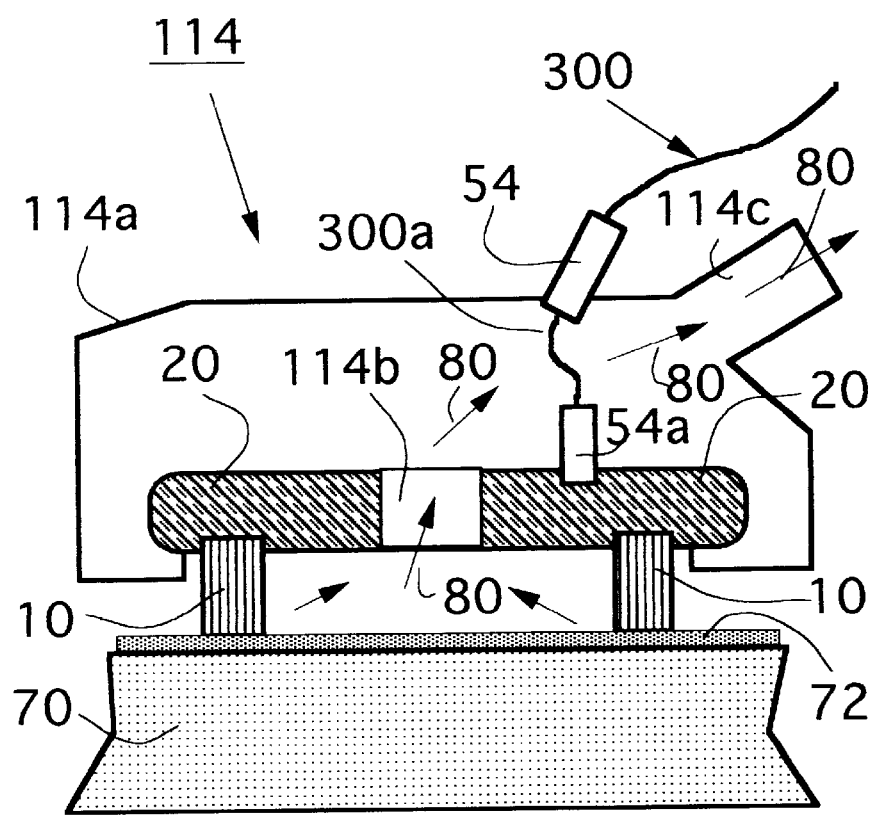
FIG. 14 illustrates a schematic, partially omitted, enlarged cross-sectional view of neighborhood of a cleaning head 114 as shown in FIG. 13, explaining tenth preferred embodiment of the present invention.

Referring to FIG. 13 and FIG. 14, eighth preferred embodiment of the invention is explained in which a cleaning apparatus of the invention is applied to a vacuum cleaner.

As shown in FIG. 13, the vacuum cleaner is roughly comprised of a cleaning tool 160, a main cleaner body 500, a flexible hose 330 and an optical fiber cable (or optical fiber) 300. The cleaning tool 160 is further comprised of a cleaning head (or nozzle, hood, suction inlet) 114 and a tube type handle (or wand) 340. The cleaner body 500 in the body casing accommodates in a motor 500b, a fan 500c rotating by the motor 500b, a dust keeping means (dust bag, dust case) 500a, a light source 200 to emit short wavelength rays, a light control circuit device 46 and wheel s (or casters) 500d for the cleaner body 500 to move easily on an substance to be cleaned such as floor and carpet. The cleaning head 114 accommodates a transparent brush supporter 20 and a group of brushes 10 with photocatalyst. The flexible hose 330 is connected with a terminal of the handle (or wand) 340 in a terminal of the hose 330 and a vacuum inlet of the cleaner body 500 in another terminal of the hose 330.

The optical fiber cable 300 capable of transmitting short wavelength rays is connected optically with the light source 200 via an optical connector 55 at a terminal of the optical fiber cable 300 and the cleaning head 114 via another optical connector 54 at another terminal of the optical fiber cable 300. Accordingly, Short wavelength rays emitted from the light source 200 housed in the cleaner body is transmitted to the transparent brush supporter 20 housed in the cleaning head 114 via the optical fiber cable 300 and radiate the photocatalyst brushes 20 to activate photocatalyst.

Therefore, when the fan 500c is rotating according to rotation of the motor 500b, an air pressure in a forward of the fan 500c is decreased and a dirty component 72 on the floor or the carpet is forced to sucked together with an air from the cleaning head 114 and the dirty component 72 is gathered inside the dust bag or dust case 500a through the hollow of the hand e 340, the flexible hose 330. Arrows 80 indicate air flows.

In FIG. 14 showing an enlarged detail of the cleaning head 114, the cleaning head 114 is comprised of the head case 114a, the transparent brush supporter 20 having the group of photocatalyst brushes 10 and a suction hole 114b, a connecting pipe 114c to connect the handle 340 (shown in FIG. 13) a detachable optical connector 54a to connect between the brush supporter 20 and an optical fiber 300a. The cleaning head 114 accommodates the brush supporter 20 with photocatalyst brushes 10 in the head case 114a and it is constructed to keep air tightness, when the photocatalyst brushes 10 contact or approach to the floor 70 (or carpet, etc.). The photocatalyst brushes 10 are the fibers including many photocatalyst particles 10 and they are fixed in a bottom of the brush supporter 20 as shown in FIG. 5.

Referring again to FIG. 13 and FIG. 14, the optical fiber cable 300 extended from the optical fiber connector 55 in one end is connected to the optical fiber connector 54 in another end fixed at the head case 114. The short optical fiber 300 is optically connected between the optical fiber connector 54 and the optical fiber connector 54a.

Therefore, the dirty component 72 contacted or adhered on the surface of the cleaned substance 70, for an example, floor are forced to remove from the surface by contacting (or sweeping, brushing) of the photocatalyst brushes 10 and moves to upper portion of the head case 11 4a via the suction inlet 114b of the brush supporter 20 and goes out from the connecting pipe 11 4c according to air f low (see arrow 80). Short wavelength rays transmitted in the cleaning head 114 is transmitted to the transparent brush supporter 20 and radiate the photocatalyst brushes 10. Since the photocatalyst brushes 10 are activated by radiation of the short wavelength rays, the dirty component 72 contacted or approached with the activated photocatalyst brushes 10 is oxidized or reduced so as to clean up.

EMBODIMENT NO.9

Figure 15:
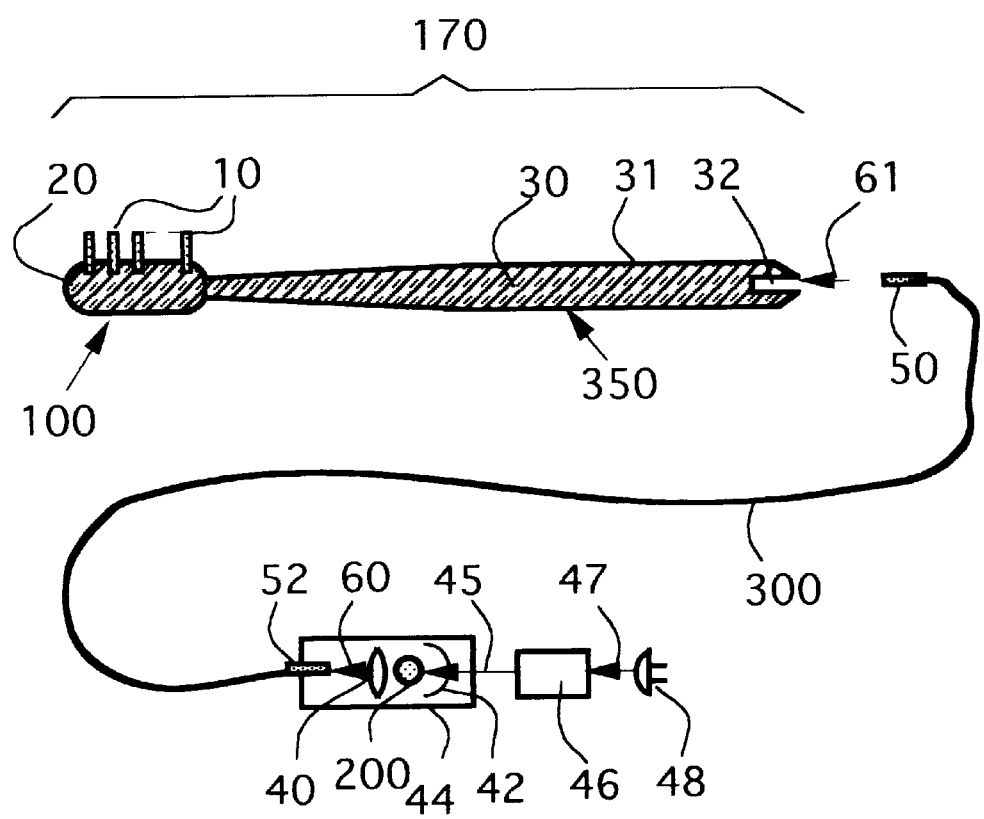
FIG. 15 illustrates a conceptional cross-sectional view, explaining eleventh preferred embodiment of the present invention, in which the invention may be applied to a dental cleaner.

FIG. 15 shows ninth preferred embodiment of the invention, in which a cleaning apparatus of the invention may be applied to a dental cleaner or tooth brushing apparatus.

As shown in FIG. 15, the dental cleaner is roughly comprised of a teeth brushing tool 170, a light source 200 to emit short wavelength rays (UV rays, etc.), a light control circuit device 46 and an optical fiber 300 to transmit UV light rays. The tooth brushing tool 170 is further comprised of a cleaning head 100 having a transparent brush supporter 20 to fix brushes10 with photocatalyst and a handle 350 having a transparent rod 30 of taper shape in cross-section to transmit UV light rays, a light reflecting sheath 31 to reflect UV light rays and a light inlet 32. The optical fiber 300 has an optical connector 50 in an end and another optical connector 52 in another end. The optical fiber 300 is connected detachably to the light inlet 32 of the transparent rod 30 in an end via the optical connector 50 and to a light incident inlet of a lamp house 44 via the optical connector 52.

Short wavelength rays 60 emitted from the light source 200 is incident to the optical fiber 300 via a lens 40 and the optical connector 52 and they are transmitting in the optical fiber 300 and they become output short wavelength rays 61. The output rays 61 are incident to the transparent handle 30 of the tooth brushing tool 350 via the optical connector 50 and they 61 are transmitting in the transparent handle 30 and are transmitting to the cleaning head 100. The short wavelength rays 61 incident to the cleaning head 100 is radiate the photocatalyst brushes 10, in which photocatalyst component is activated.

In case a teeth brushing is done by using the tooth brushing tool 170 to surface of teeth, gums, and between teeth, etc. such dirty components inside a mouse are easily dissolved and removed according to photocatalyst action as residue or garbage of food, bacteria, molds, plaque, scale and nicotine/tar due to smoking.

EMBODIMENT NO.10

Figure 16:
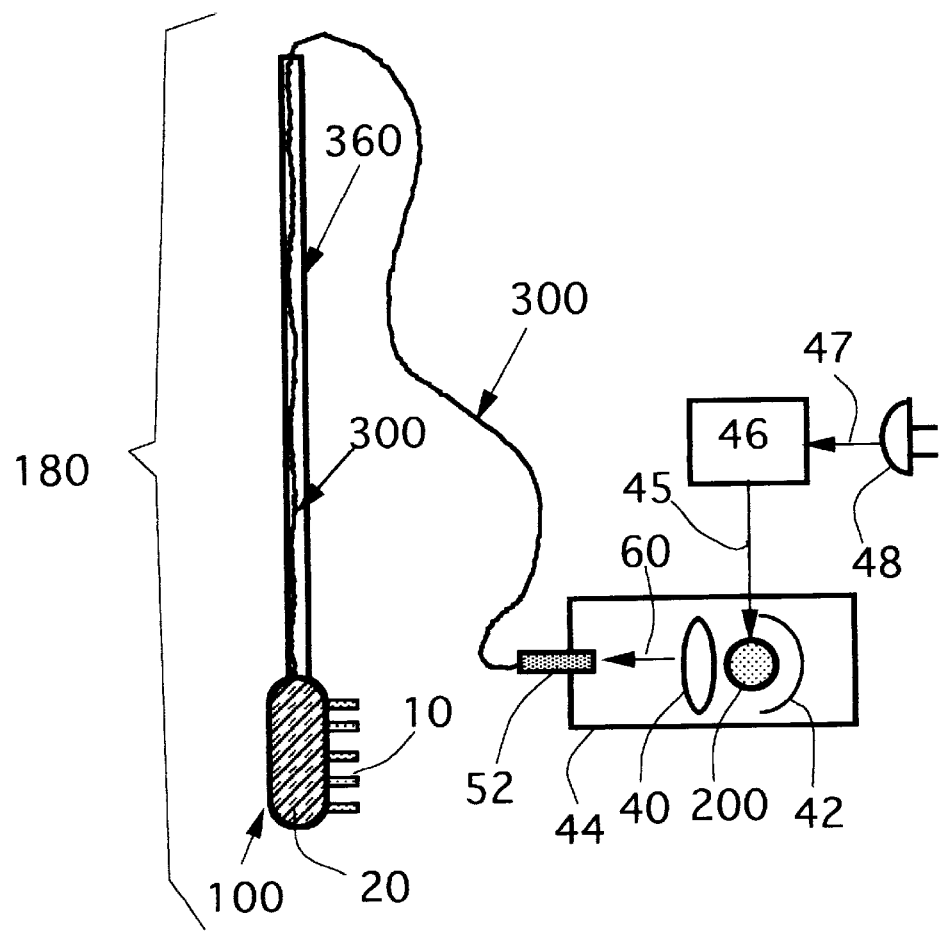
FIG. 16 illustrates a conceptional cross-sectional view, explaining twelfth preferred embodiment of the present invention in which the invention may be applied to a dental cleaner.

FIG. 16 shows tenth preferred embodiment of the invention, in which a cleaning apparatus of the invention may be applied to a dental cleaner or tooth brushing apparatus, similarly to the embodiment NO.9 previously explained.

As shown in FIG. 16, the dental cleaner is roughly comprised of a teeth brushing tool 180, a light source 200 to emit short wavelength rays (UV rays, etc.), a light control circuit device 46 and an optical fiber 300 to transmit UV light rays. The teeth brushing tool 180 is further comprised of a cleaning head 100 having a transparent brush supporter 20 to fix brushes 10 with photocatalyst and a handle 360 of tube connected or jointed to the cleaning head 100 at an end. The optical fiber 300 at an end is connected with the cleaning head 100, it is passing through an inside of the tube 360 (handle), it is going outside and finally at another end it is connected with a light output inlet of a lamp house 44 by a detachable optical connector 52. Since an optical fiber cable includes multiple of optical fibers, an optical cable may be used instead of an optical fiber, or vice versa in the above mentioned embodiments.

It is to be understood that the forgoing description is preferred embodiments of the invention and that various changes, modifications, combinations, or equivalents may be made in the invention without departing from the spirit and the scope of the present invention and the appended claims.

What is claimed is:

1. A cleaning apparatus using photocatalyst comprising:

brushing means having a plurality of brushes and a brush supporter to support said brushes;

a plurality of photocatalyst elements; and wherein at least one of said brushes is composed of a core and said core includes a plurality of said photocatalyst elements.

2. The cleaning apparatus according to claim 1:

wherein said brush supporter is made of transparent material; and wherein said brush supporter has at least a light-reflecting layer.

3. The cleaning apparatus according to claim 1, further comprising:

at least a light source emitting light capable of activating said photocatalyst elements.

4. The cleaning apparatus according to claim 1, further comprising:

at least a light source emitting light capable of activating said photocatalyst elements; and wherein said light source is composed of at least a light-emitting semiconductor.

5. The cleaning apparatus according to claim 1, further comprising:

at least a light source emitting light capable of activating said photocatalyst elements;

wherein said light source is composed of at least a light emitting semiconductor; and wherein said light emitting semiconductor is included in said brushing means.

6. The cleaning apparatus according to claim 1, further comprising:

at least a light guide member or optical fiber having a first end for light entrance and a second end for light exit; and wherein light input into said first end is transmitted to said second end and is output to said brushing means.

7. A cleaning apparatus using photocatalyst comprising:

brushing means having a plurality of brushes and a brush supporter to support said brushes;

a plurality of photocatalyst elements; and wherein at least one of said brushes is composed of a core and a sheath to cover said core, and said sheath includes a plurality of said photocatalyst elements.

8. The cleaning apparatus according to claim 7:

wherein said brush supporter is made of transparent material; and wherein said brush supporter has at least a light-reflecting layer.

9. The cleaning apparatus according to claim 7, further comprising:

at least a light source emitting light capable of activating said photocatalyst elements.

10. The cleaning apparatus according to claim 7, further comprising:

at least a light source emitting light capable of activating said photocatalyst elements; and wherein said light source is composed of at least a light-emitting semiconductor.

11. The cleaning apparatus according to claim 7, further comprising:

at least a light source emitting light capable of activating said photocatalyst elements;

wherein said light source is composed of at least a light emitting semiconductor; and wherein said light emitting semiconductor is included in said brushing means.

12. The cleaning apparatus according to claim 7, further comprising:

at least a light guide member or optical fiber having a first end for light entrance and a second end for light exit; and wherein light input into said first end is transmitted to said second end and is output to said brushing means.

13. A cleaning apparatus using photocatalyst comprising:

brushing means having a plurality of brushes and a brush supporter to support said brushes;

a plurality of photocatalyst elements;

said brush supporter being made of transparent material;

a plurality of light diffusing elements embedded in said brush supporter; and wherein said photocatalyst elements are included in at least one of said brushes.

14. The cleaning apparatus according to claim 13:

wherein at least one of said brushes is composed of a core or a combination of a core and a sheath to cover said core; and said core and/or said sheath includes said photocatalyst elements.

15. The cleaning apparatus according to claim 13:

wherein said brush supporter has at least a light-reflecting layer.

16. The cleaning apparatus according to claim 13:

wherein said light diffusing elements are composed of light reflecting pigments; and wherein said light reflecting pigments are made of the material selected from the group consisting of titanium oxide, aluminum, calcium carbonate and barium carbonate.

17. The cleaning apparatus according to claim 13, further comprising:

at least a light source emitting light capable of activating said photocatalyst elements.

18. The cleaning apparatus according to claim 13, further comprising:

at least a light source emitting light capable of activating said photocatalyst elements; and wherein said light source is composed of at least a light-emitting semiconductor.

19. The cleaning apparatus according to claim 13, further comprising:

at least a light source emitting light capable of activating said photocatalyst elements;

wherein said light source is composed of at least a light emitting semiconductor; and wherein said light emitting semiconductor is included in said brushing means.

20. The cleaning apparatus according to claim 13, further comprising:

at least a light guide member or optical fiber having a first end for light entrance and a second end for light exit; and wherein light input into said first end is transmitted to said second end and is output into said brushing means.

* * * * *